United States Patent [19]

Raines

[11] 4,246,932

[45] Jan. 27, 1981

[54] MULTIPLE ADDITIVE VALVE ASSEMBLY

[75] Inventor: Kenneth Raines, Bethlehem, Pa.

[73] Assignee: Burron Medical, Inc., Bethlehem, Pa.

[21] Appl. No.: 86,178

[22] Filed: Oct. 18, 1979

[51] Int. Cl.³ ............................................. F16K 15/14
[52] U.S. Cl. .................................... 137/512; 417/566;
128/274; 251/367
[58] Field of Search ........................ 137/512; 417/566;
128/272, 274, 276, 214 B, 205.13, 205.16,
207.23; 251/367

[56] References Cited

U.S. PATENT DOCUMENTS

| | | | |
|---|---|---|---|
| 1,638,114 | 8/1927 | Dunlap et al. | 137/512 |
| 2,138,605 | 11/1938 | Landis | 137/512 |
| 3,119,411 | 1/1964 | Bock et al. | 137/512 |
| 3,485,419 | 12/1969 | Taylor | 417/566 |
| 3,559,644 | 2/1971 | Stoft et al. | 128/274 |
| 3,572,375 | 3/1971 | Rosenberg | 128/274 |
| 3,902,516 | 9/1975 | Rudolph | 137/512 |
| 3,981,636 | 9/1976 | Aoki et al. | 417/566 |
| 4,096,997 | 6/1978 | Larson | 137/512 |
| 4,180,377 | 12/1979 | Itakura | 417/566 |

Primary Examiner—William R. Cline
Assistant Examiner—H. Jay Spiegel
Attorney, Agent, or Firm—Shoemaker and Mattare, Ltd.

[57] ABSTRACT

A multiple valve assembly for use in the medical field includes a pair of flexible valve discs which are essentially co-planar with each other. A pair of tube connectors are oriented to be at an essentially right angle with respect to each other, and fluid communication between the interior of a hollow body and the tube connectors is controlled by the valve discs. An aspiration procedure has one valve disc in an open position and the other valve disc in an occluding position, and an injection procedure reverses the positions of the valve discs.

12 Claims, 5 Drawing Figures

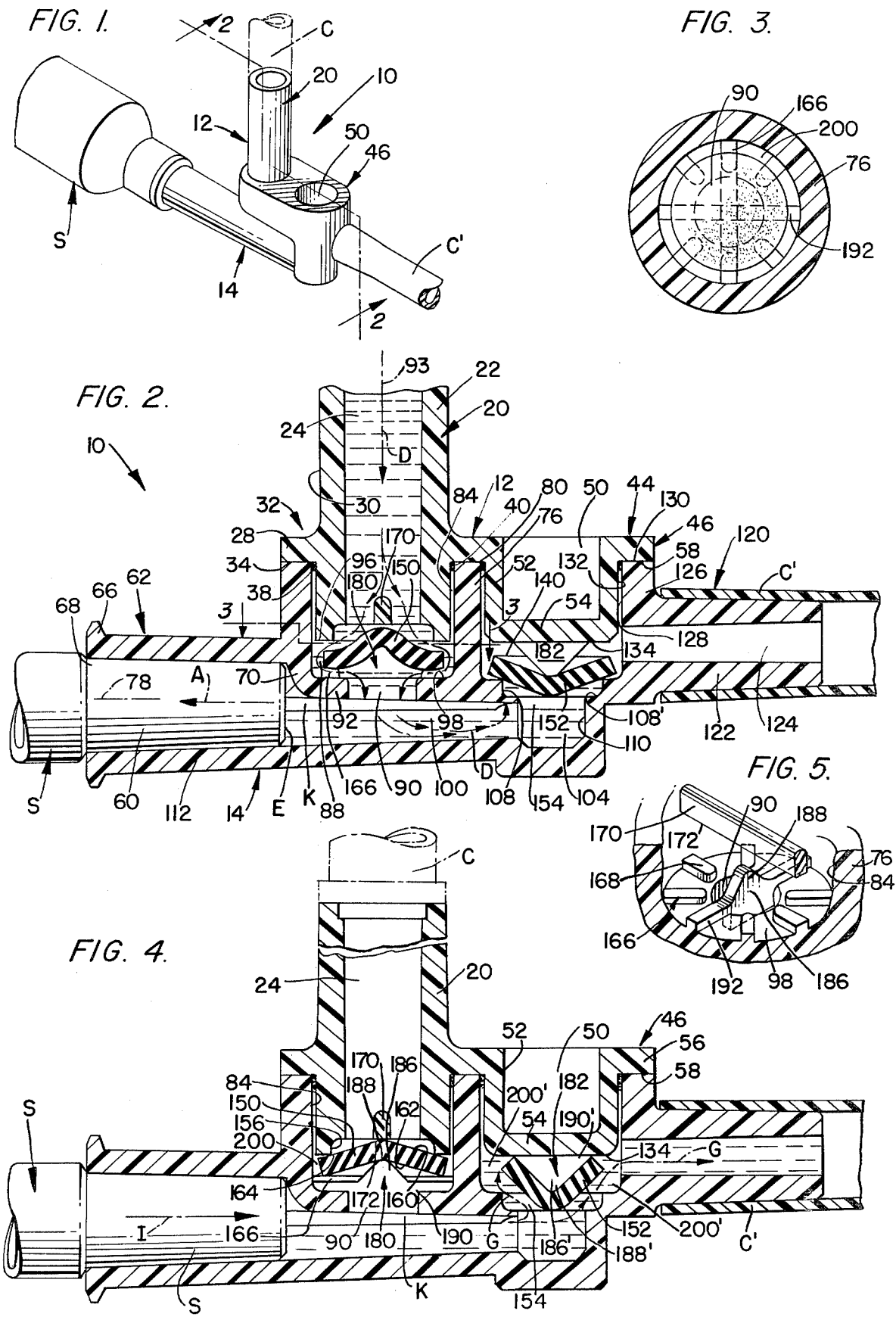

MULTIPLE ADDITIVE VALVE ASSEMBLY

BACKGROUND OF THE INVENTION

The present invention relates in general to valves, and, more particularly, to valve assemblies used in the medical field.

The medical field often requires withdrawal of fluid from one container and injection of a precise dosage of that fluid into another container. Such fluid transfer procedures are often carried out using syringes, and the like.

Often, medical fluid transfer procedures utilize valve assemblies. Examples of such devices are disclosed in U.S. Pat. Nos. 3,010,583, 3,886,937 and 4,084,606.

The valve assemblies disclosed in the art prior to the present disclosure have several drawbacks, with the most important drawbacks being cost and difficulty of manufacturing processes used for these valve assemblies.

There is thus need of a valve assembly in the medical field which is efficiently and inexpensively manufacturable.

SUMMARY OF THE INVENTION

The device embodying the teachings of the present invention has fewer parts than those valve assemblies known prior to this disclosure, and those parts are arranged to be easily and efficiently positioned. The valve assembly embodying the teachings of the present invention is thus manufacturable in an efficient, inexpensive manner as compared to other devices.

The valve assembly includes a body unit and a top unit sonically welded together. The unit has a pair of tubing connectors which are positioned at a right angle to each other, and an injection means coupling means positioned to be aligned with one of the tubing connectors.

The device includes a pair of valve discs which are positioned to be in a common horizontally disposed plane with each other.

Valve disc biasing means abut the discs and keeper means are positioned to abut one of the discs to retain that disc in position in the event fluid pressure exceeds predetermined values. The natural resiliency of both discs biases those discs toward occluding positions.

In an aspiration procedure, one valve disc flexes to open a fluid flow path between a fluid source and the interior of the valve assembly via one of the two tubing connectors, while the other valve disc is pressed more tightly into an occluding position to seal the interior of the valve assembly from the other tubing connector.

In an injection procedure, the other valve disc is biased to cause flexing of same to open a fluid flow path between the interior of the valve assembly and a fluid receptacle via the other tubing connector, while the first valve disc is pressed more tightly into an occluding position to seal the interior of the valve assembly from the fluid source.

An injection means, such as a syringe, or the like, provides sufficient pressure gradients to operate the valve assembly.

The valve discs are co-planar and are thus easily and quickly positioned during the manufacturing process. Only two valves are needed for the presently disclosed assembly, and thus cost savings and manufacturing efficiency are achieved. Rapid assembly of the device is possible as compared to other heretofore known devices, again contributing to cost of savings.

OBJECTS OF THE INVENTION

It is, therefore, a main object of the present invention to provide a medical valve assembly which is efficiently manufacturable.

It is another object of the present invention to provide a medical valve assembly which is less costly to manufacture than heretofore known devices.

It is yet another object of the present invention to provide a medical valve assembly which has fewer parts than heretofore known devices.

It is still another object of the present invention to provide a medical valve assembly which is quickly assembled.

These together with other objects and advantages which will become subsequently apparent reside in the details of construction and operation as more fully hereinafter described and claimed, reference being had to the accompanying drawings forming part hereof, wherein like reference numerals refer to like parts throughout.

BRIEF DESCRIPTION OF THE DRAWINGS

FIG. 1 is a perspective showing the device embodying the teachings of the present invention.

FIG. 2 is a view along line 2—2 of FIG. 1.

FIG. 3 is a view along line 3—3 of FIG. 2 showing the device embodying the teachings of the present invention in a fluid aspirating condition.

FIG. 4 is the device embodying the teachings of the present invention in a fluid injecting condition.

FIG. 5 is a perspective showing a support for one of the valve discs included in the device embodying the teachings of the present invention.

DETAILED DESCRIPTION OF THE INVENTION

Shown in FIG. 1 is a valve assembly 10 fluidly connecting a syringe S to a pair of conduits C and C' which are oriented at right angles to each other. The assembly 10 is easily manufactured and this is inexpensive compared to devices presently available.

The assembly 10 is best shown in FIGS. 2 and 4, and attention is directed thereto. The assembly 10 includes a top 12 and a bottom 14 which are sonically welded together in the preferred embodiment.

The top 12 includes a tubular tubing connector 20 having a tubular body 22 with a bore 24 defined longitudinally thereof. A shoulder 28 is defined to extend radially outward of the outer surface 30 of the body near end 32 thereof. An energy director element is also defined on the body closely adjacent the undersurface 34 of the shoulder 28. The energy director element extends radially outward of the surface 30 and has a radial extent less than that of the shoulder 28 so that the shoulder and the energy director form a surface which is stepped inwardly toward the lower end 32. The energy director melts upon application of ultrasonic, or sonic, energy and thus forms joints, such as joints 38 and 40 shown in FIG. 2.

As shown in FIG. 2, the shoulder 28 is a portion of a platform element 44. The platform element 44 is elliptical in peripheral outline with the shoulder 28 being located at one end of the ellipse, with the other end of the ellipse being denoted by the reference indicator 46. As best shown in FIGS. 1, 2 and 4, a blind-ended bore 50 is defined in the platform element 44 in end 46. The bore has a cylindrical wall 52 and a bottom 54, with the wall 52 being spaced from the tube wall 20. The platform has an overhang 56 which has an undersurface 58 co-planer with undersurface 34 of the shoulder 28. Weld joints are formed under surface 58 in a manner similar to the joints 38 and 40, and thus an energy director element is positioned at this location also.

The bottom 14 includes an inwardly tapered bore 60 defined in one end 62 thereof for accommodating a portion of an injection means, such as syringe S having a cannula K thereon. A peripheral lip 66 surrounds entrance port 68 of the end 62. A rounded shoulder 70 is defined within the bore 60 to serve as a stop for the injection means portion leading end E. This stop means is positioned to orient leading end E at or near the end 32 of the tubing connector.

A tubular wall 76 is positioned on the bottom 14 to extend at a right angle with respect to longitudinal centerline 78 of bottom 14. The wall 76 has a top rim 80 which abuts the undersurface of the platform element and has an inner surface 84 which is welded to the outer surface 30 of the connector wall 20 by joints 38 and 40.

As shown in FIGS. 2 and 4, a pocket 88 is defined in the bottom 14 to accommodate end 32 of the connector 20. The outer surface of this pocket forms the stop means for end E of the injection means. A port 90 is defined in wall 92 of the bottom 14 to be centered on longitudinal centerline 93 of the connector 20 and the bore 24. The inside of the bottom section 14 can thus be placed in fluid communication with the bore 24 via port 90.

The end 32 has a rim 96 which is spaced from surface 98 of the wall 92 which forms the bottom of the pocket 88.

A channel 100 is fluidly connected to bore 60 and to port 90 and is an extension of the bore 60 and is at right angles to the port 90. An accumulator chamber 104 is defined at the end of the channel 100 remote from the bore 60. The chamber 104 is tubular and is aligned with the bore 50. Wall 112 forms the bottom wall of the body 14, and has a counterbore 108' defined therein to partially surround the bore 110.

The body 14 has a second end 120 which includes a wall 122 having a bore 124 which is tapered inwardly toward bore 60. A shoulder 126 is defined on the wall 122 and has inner surface 128 and rim 130 thereon. The rim 130 abuts the undersurface of the platform element and the inner surface 126 is welded to outer surface 132 of the wall 52 by joints similar to joints 38 and 40. The tubing C' is jam fit on the wall 122 to be fluidly connected to the bore 124.

As shown in FIGS. 2 and 4, bottom surface 134 of the blind-ended bore bottom 54 is spaced from the counterbores 108 and 108', thereby defining a passageway chamber 140 which can be placed in fluid communication with the bore 124 and with the chamber 104. The bore 124 and the chamber 104 are disposed at a right angle to each other, and hence the bore 124 is at a right angle with respect to the chamber 140.

Fluid paths are thus establishable between the bore 124 and the bores 24 and 60 when desired, as will be discussed below.

A pair of horizontally aligned valve discs 150 and 152 are seated on tube connector end 32 and in portal 154 of the accumulator chamber 104, respectively. In the preferred embodiment, the valve discs 150 and 152 are essentially circular in peripheral outline and are cupola-shaped in elevation. As will be discussed below, the discs are flexible and control flow of fluid through the assembly 10. As shown in FIG. 4, the valve disc 150 is located to cover counterbore 156 defined in tube connector end 32. The disc 150 has an upper surface 160 and a lower surface 162, with upper surface 160 abutting inner edge 164 of the end 32 to occlude the tube connector and prevent fluid communication between the bore 24 and the port 90. The disc 150 is seatable on a plurality of disc supports 166 which are tombstone-shaped extended elements having an upper surface 168 on which the disc lower surface 162 rests in the FIG. 2 configuration. The upper surfaces 168 of the supports are all co-planar and horizontally disposed so that the disc is held in position adjacent the port 90 in a horizontal orientation. The disc supports are spaced apart to define fluid paths therebetween so that fluid can flow therepast.

A disc immobilizer 170 is integrally mounted on the inner surface of the bore 24 to extend thereacross as best shown in FIG. 5. The immobilizer has a lower surface 172 which abuts the disc upper surface to limit upward movement of that disc. The operation of the disc immobilizer will be apparent from the discussion presented below.

V-shaped disc seats 180 and 182 are mounted adjacent each disc 150 and 152 to contact the disc near the apex of the cupola-shaped disc as indicated in FIGS. 3 and 4. The disc seats include triangular projections 186 and 186' having apeces 188 and 188' and bases 190 and 190'. The disc seat 180 further includes a cross brace 192 best shown in FIGS. 3 and 5 as extending across the pocket 88 and being integrally attached to inner surface 84 thereof. The cross brace supports the projection 186 thereon. The projection 186' is mounted on surface 134 of the blind-ended bore base 54.

As shown in FIGS. 3 and 4, a flow path is defined around the discs when those discs are appropriately positioned. Thus, circumferential channels 200 and 200' are defined about discs 150 and 152, respectively.

The natural resiliency of the discs combines with the disc seats to bias the discs into a flow path occluding position. Thus, without any other bias being applied thereto, the disc 150 occludes the bore 24, or assumes the FIG. 4 position, and the disc 152 assumes the FIG. 2 position to occlude the portal 154. However, as will be evident from this disclosure, the discs are biased toward and away from such relaxed positions when suitable.

An aspiration procedure can be conducted using the syringe S by operating such syringe to produce a pressure gradient in the assembly 10 as indicated by the arrow A in FIG. 2. Such pressure gradient acts on the disc 150 to bias that disc from the FIG. 4 orientation into the FIG. 2 orientation. When the pressure on the disc is sufficient, that disc flexes into the FIG. 2 position, thereby establishing the channel 200 and fluidly connecting the interior of the assembly 10 with tubing C via the tubing connector. The pressure gradient causes flow through the tubing connector into the interior of the assembly 10. Of course, the disc 150 is not flexed until the pressure gradient caused by the syringe reaches a predetermined level. The material and dimensions of the disc can be selected to establish any desired value and range for this opening pressure gradient. The flow established by such pressure gradient through the tubing connector 20 and into cannula K is indicated in FIG. 2 by arrows D. The supports 166 support the disc in the FIG. 2 position to prevent that disc from occluding the port 90 even when the pressure gradient established by the syringe reaches very high values. Flow is thus established around the disc 150.

As can be seen in FIG. 3, the pressure gradient indicated by arrow A biases the disc 152 onto the disc seat defined by the edges of the counterbores 108 and 108'. Thus, fluid will be prevented from passing the disc 152 in the direction of arrow A in FIG. 3, but will be permitted to move in the direction of arrow D. In this manner, fluid can be drawn from a source (not shown) into the assembly 10.

Thus, in an aspiration step, the valve 150 is open and valve 152 is closed.

An injection procedure is carried out by reversing the above-described procedure so that fluid moves in the direction of arrow I in FIG. 4. The pressure gradient established by this procedure acts on the valve discs 150 and 152, and moves those discs so that the disc 150 abuts the rim 96 and thus occludes the bore 24, and, when the pressure is sufficient, moves the disc 152 away from the disc seat to establish flow path 200' as shown in FIG. 4. The pressure must be sufficient to overcome the natural resiliency of the disc 152 and force the peripheral edge thereof over outer surface 220 of the projection 186'. The projection 186' supports the valve disc and prevents undesired movement thereof so that the disc will return to the occluding position of FIG. 2 when the pressure gradient thereacross drops below a prescribed value. Fluid thus passes through the flow channel 200' in moving from the passage 100 to the bore 124 via chamber 104 and portal 154 as indicated by arrows G in FIG. 4. The fluid drawn into the assembly by the above-discussed aspiration procedure is thus forced into a receiver (not shown) via the bore 124 and tubing C' on the injection step. On the injection step, valve 150 is closed and valve 152 is open.

When the pressure drops below a specified value, the valve discs return to their natural positions. Thus, when aspiration pressure is below a specified value, the valve disc 150 is closed, and when the injection pressure is below a specified value, the valve disc 152 is closed.

The holddown rib 170 prevents the valve disc 150 from being forced back into the bore 24 when high injection pressure is applied. The cross brace is sized to permit fluid flow therepast into the port 90.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A multiple valve assembly for use in transferring fluid in medical applications, comprising:
   an elongate hollow body portion having means on one end portion thereof for accommodating a fluid pressure establishing means, a first tube connector on another end portion thereof, a tube connector accommodating means between said ends and oriented at a right angle with respect to said first tube connector, an outer wall, a first port defined in said outer wall to fluidly connect said tube connector accommodating means with the interior of said hollow body portion and a second port defined in said wall to fluidly connect said first tube connector with the interior of said hollow body;
   a top portion affixed to said body portion and including a second hollow tube connector positioned to be accommodated in said body portion tube connector accommodating means so that fluid communication between the inside of said second hollow tube connector and said body portion first port is possible;
   a pair of flexible valve discs mounted on said hollow body portion, said valve discs being co-planar with each other and oriented at a right angle with one of said tube connectors and in a plane which is substantially parallel with the other one of said tube connectors, one of said valve discs positioned to occlude said second tube connector and the other valve disc being positioned to occlude said second port; and
   valve disc biasing means adjacent each of said valve discs for biasing said valve discs toward an occluding position.

2. The multiple valve assembly defined in claim 1 further including stop means located adjacent said one valve disc to prevent said one valve disc from being forced into said tube connector accommodating means.

3. The multiple valve assembly defined in claim 1 further including a fluid accumulator defined in said body portion adjacent said second port.

4. The multiple valve assembly defined in claim 1 further including ultrasonic welds connecting said top portion to said body portion.

5. The multiple valve assembly defined in claim 1 wherein said valve discs are circular in peripheral shape.

6. The multiple valve assembly defined in claim 1 wherein said valve disc biasing means includes a pair of triangular bodies each having a base and an apex with said apex abutting a valve disc.

7. The multiple valve assembly defined in claim 6 wherein one of said biasing means further includes a crossbrace attached to said body portion and positioned to support one of said valve discs adjacent said first port.

8. The multiple valve assembly defined in claim 1 further including a stop shoulder defined inside said hollow body portion for defining a limit for which a fluid pressure defining means can be inserted into said hollow body portion.

9. The multiple valve assembly defined in claim 1 further including tubes jam fit onto said tubing connectors.

10. The multiple valve assembly defined in claim 9 further including a syringe coupled to said body one end portion.

11. The multiple valve assembly defined in claim 1 wherein said ports are spaced from each other.

12. The multiple valve assembly defined in claim 1 wherein said body portion ends are in spaced parallelism with each other.

* * * * *